(12) United States Patent
Oikawa et al.

(10) Patent No.: US 9,317,716 B2
(45) Date of Patent: Apr. 19, 2016

(54) PRIVACY PROTECTION-TYPE DATA PROVIDING SYSTEM

(71) Applicant: HITACHI, LTD., Tokyo (JP)

(72) Inventors: Michio Oikawa, Tokyo (JP); Yoshinori Sato, Tokyo (JP); Keisei Fujiwara, Tokyo (JP); Kunihiko Harada, Tokyo (JP); Yumiko Yokohari, Tokkyo (JP); Tatsuya Nakae, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/283,366

(22) Filed: May 21, 2014

(65) Prior Publication Data

US 2014/0351946 A1    Nov. 27, 2014

(30) Foreign Application Priority Data

May 22, 2013   (JP) ................... 2013-107582

(51) Int. Cl.
*G06F 21/00* (2013.01)
*G06F 21/62* (2013.01)
*G06F 19/00* (2011.01)

(52) U.S. Cl.
CPC .......... *G06F 21/6254* (2013.01); *G06F 19/322* (2013.01)

(58) Field of Classification Search
CPC combination set(s) only.
See application file for complete search history.

(56) References Cited

U.S. PATENT DOCUMENTS

2003/0208457 A1*  11/2003  Iyengar ........................... 707/1
2004/0199781 A1*  10/2004  Erickson et al. ............. 713/200
2007/0061393 A1*  3/2007  Moore ........................... 709/201
2011/0016482 A1*  1/2011  Tidwell ................. G06Q 30/00
                                                            725/14
2013/0138698 A1   5/2013  Harada et al.
2015/0033356 A1*  1/2015  Takenouchi .................... 726/26

FOREIGN PATENT DOCUMENTS

JP   2012-003323 A   1/2012
JP   2013-080375 A   5/2013
JP   2013-161428 A   8/2013

OTHER PUBLICATIONS

Harada et al., "Reducing Amount of Information Loss in k-Anonymization for Secondary Use of Collected Personal Information", 2012 Services Research and Innovation Institute Global Conference, 2012, pp. 61-69.

* cited by examiner

*Primary Examiner* — Jason Lee

(74) *Attorney, Agent, or Firm* — Mattingly & Malur, P.C.

(57) ABSTRACT

An information providing apparatus for collecting data including personal information and distributing the data to a user terminal performs anonymization processing for converting data, which an individual who is an owner of personal information allows to use, into data with which the individual cannot be identified using multiple parameters, thus generating multiple anonymized data protecting the, privacy of the individual. Since each of the anonymized data is anonymized using a different parameter, the amount of information of each of the anonymized data is different. Then, when a request is received from a user terminal, anonymized data that can be provided to the user are identified from among multiple generated anonymized data on the basis of the reliability of the user who uses the user terminal.

10 Claims, 11 Drawing Sheets

FIG. 3

PRIVACY PROTECTION CONDITION INFORMATION

| PROTECTION CONDITION | SETTING VALUE |
|---|---|
| PERSONAL INFORMATION RANGE | DATA FIELD TYPES: ID, NAME, ADDRESS, ZIP CODE, TELEPHONE NUMBER, MAIL ADDRESS, DATE OF BIRTH, AGE, SEX |
| DELETION ITEMS | DATA FIELD TYPES: ID, NAME, ZIP CODE, TELEPHONE NUMBER, MAIL ADDRESS, DATE OF BIRTH, DATES OF ADMISSION TO AND DISCHARGE FROM HOSPITAL |
| CONVERSION ITEMS | — |
| PROTECTION ITEMS | DATA FIELD TYPES: ADDRESS, AGE, SEX, NAME OF DISEASE, NAME OF OPERATION |
| MINIMUM VALUE OF k VALUE | 10 |
| USAGE PERMISSION | PERMISSION TABLE LINK DESTINATION |

USAGE CONDITION INFORMATION

TOTAL RELIABILITY = 10

10

| DATA SET DEPENDING ON PURPOSES | DATA FIELD TYPES | NUMBER OF YEARS DATA ARE OBTAINED | ANONYMIZATION DATA SET | K VALUE | USAGE PRICE |
|---|---|---|---|---|---|
| DIABETES SET | ADDRESS, AGE, SEX, NAME OF DISEASE, NAME OF MEDICINE, NAME OF OPERATION, BLOOD PRESSURE, HbA1c | ALL YEARS | DATA SET A | 10 | 10,000,000 |
| | | | DATA SET B | 100 | 5,000,000 |
| | | | DATA SET C | 500 | 1,000,000 |
| | | FIVE YEARS | | ... | ... |
| | | ONE YEAR | | ... | |
| RESPIRATORY SYSTEM SET | | ... | | | |
| ... | | | | | |
| ANY GIVEN SET | | | | | |

⋮

TOTAL RELIABILITY = 3

10

| DATA SET DEPENDING ON PURPOSES | DATA FIELD TYPES | NUMBER OF YEARS DATA ARE OBTAINED | ANONYMIZATION DATA SET | K VALUE | USAGE PRICE |
|---|---|---|---|---|---|
| DIABETES SET | ADDRESS, AGE, SEX, NAME OF DISEASE, NAME OF MEDICINE, NAME OF OPERATION, BLOOD PRESSURE, HbA1c | ALL YEARS | DATA SET C | 500 | 1,000,000 |
| | | FIVE YEARS | DATA SET C | 500 | 1,000,000 |
| | | ONE YEAR | DATA SET C | 500 | 1,000,000 |
| RESPIRATORY SYSTEM SET | | ... | | ... | |
| ... | | | | | |
| ANY GIVEN SET | | | | | |

⋮

USER RELIABILITY INFORMATION

| ITEMS | NATIONAL HOSPITAL A | PRIVATE UNIVERSITY HOSPITAL B | PHARMACEUTICAL COMPANY C | FOOD COMPANY D | COSMETICS COMPANY E |
|---|---|---|---|---|---|
| PUBLIC BENEFIT | 100 | 80 | 50 | 30 | 20 |
| JIS Q 15001:2006 | — | — | ○ | — | ○ |
| INFORMATION LEAKAGE ACCIDENT | 1 | 0 | 0 | 2 | 0 |
| TRANSACTION HISTORY | 30 | 10 | 10 | 0 | 2 |
| TOTAL RELIABILITY | 9 | 8 | 7 | 1 | 6 |

*FIG. 7*

USAGE PERMISSION TABLE 24

| PATIENT ID | RELIABILITY A | RELIABILITY B | RELIABILITY C | RELIABILITY D |
|---|---|---|---|---|
| 00001 | 10 | 10 | 50 | 100 |
| 00002 | 2 | 10 | 30 | 100 |
| ... | | | | |
| 10005 | 100 | 200 | — | — |
| ... | | | | |

FIG. 12

DATA CATALOG

1. DIABETES DATA SET

| NUMBER OF YEARS DATA ARE OBTAINED | DATA SET | INFORMATION LOSS AMOUNT | PRICE | PURCHASE |
|---|---|---|---|---|
| ALL YEARS | SET A | 0.001 | 10,000,000 | |
| | SET B | 0.008 | 5,000,000 | |
| | SET C | 0.02 | 1,000,000 | |
| FIVE YEARS | SET A | 0.002 | 8,000,000 | |
| | SET B | 0.01 | 4,000,000 | ✓ |
| | SET C | 0.02 | 800,000 | |
| ONE YEAR | SET A | 0.01 | 3,000,000 | |
| | SET B | 0.05 | 700,000 | |

OK   CANCEL

DATA SAMPLE

1. DIABETES DATA SET

| SAMPLE | ADDRESS | AGE | SEX | NAME OF DISEASE | NAME OF MEDICINE | NAME OF OPERATION | BLOOD PRESSURE |
|---|---|---|---|---|---|---|---|
| A | OTA-KU, TOKYO | 32 | MALE | DIABETES | AMARYL | — | 170/80 |
| B | KAGAWA | 80 | MALE | DIABETES | GLUCOBAY | — | 160/100 |
| C | YOKOHAMA, KANAGAWA | 70 | FEMALE | DIABETES, HYPERTENSION | METGLUCO | ADJUSTABLE GASTRIC BANDING | 190/115 |

CLOSE

PRIVACY PROTECTION-TYPE DATA PROVIDING SYSTEM

CROSS-REFERENCE TO RELATED APPLICATIONS

This application claims the priority of Japanese Patent Application No. 2013-107582, filed on May 22, 2013, which is incorporated herein by reference in its entirety.

BACKGROUND OF THE INVENTION

1. Field of the Invention

The present invention relates to a system for providing data upon anonymizing or generalizing information about privacy in order to allow secondary usage of the data.

2. Description of the Related Art

With various kinds of progress made in information technology such as cost reduction of storages, increase in the capacities of storages, establishment of networks, and widespread use of portable information terminals, the amount of accumulated information is increasing in an explosive manner, and there is an increasing movement toward the use of so-called big data. However, among the big data, secondary usage of information about individuals is required to be used upon protecting the privacy. For example, JP-2012-3323-A "personal information disclosure support apparatus, method, and program" discloses a method for protecting the privacy by controlling a disclosure level by deriving the reliability of a recipient of the disclosure by the user on the basis of the number of accesses to a web site and management information in a case where personal information is disclosed.

When personal information is simply deleted or an ID for identifying an individual is simply replaced with another ID, there is a risk that a person may be identified by combining conditions. Therefore, k-anonymization method is known as a method for more securely protecting the privacy. In the k-anonymizationmethod, the original data are generalized so that at least k or more data having the same condition are configured to exist in a combination of designated data field types. (See K. Harada, Y. Sato and Y. Togashi, "Reducing Amount of Information Loss in k-anonymization for Secondary Use of Collected. Personal Information," Proc. of SRII Global Conference 2012, pp. 61-69.)

SUMMARY OF THE INVENTION

However, the conventional technique explained above involves the following problem, in a case where, for example, healthcare information which is extremely sensitive personal information is used. First, like JP-2012-3323-A "personal information disclosure support apparatus, method, and program", there may be a case where the disclosure range is automatically determined, there may be a case where a person may not wish to disclose his/her information, or in a case where, on the contrary, information is desired to be actively disclosed for the sake of public benefit, the user may not be able to determine the disclosure range.

When a highly publicly beneficial situation which is to be of help of many people, e.g., prevention of epidemic of infection or improvement in a method of treating a disease, as a situation for utilizing healthcare data, it is necessary to disclose and provide data which are unified to a certain level. For this reason, when the disclosure range is allowed to be determined for each user, a sufficient amount of information cannot be provided to the user of the data, and ultimately, meaningful result cannot be ultimately obtained even if the data are analyzed.

When applying the k-anonymization technique such as K. Harada, Y. Sato and Y. Togashi, "Reducing Amount of Information Loss in k-anonymization for Secondary Use of Collected Personal Information," Proc. of SRII Global Conference 2012, pp. 61-69, a useful method as to how to determine the k value which is a parameter has not yet been known, and it is necessary to have a mechanism in view of not only the security for the providing person of the data but also the convenience of the user of the data.

Accordingly, in the present invention, an information providing apparatus for collecting data including personal information and distributing the data to a user terminal performs anonymization processing for converting data, which an individual who is an owner of personal information allows to use, into data with which the individual cannot be identified using multiple parameters, thus generating multiple anonymized data protecting the privacy of the individual. Since each of the anonymized data is anonymized using a different parameter, the amount of information of each of the anonymized data is different. Then, when a request is received from a user terminal, anonymized data that can be provided to the user are identified from among multiple generated anonymized data on the basis of the reliability of the user who uses the user terminal.

According to the present invention, highly convenient data can be provided to the user of the data while protecting the privacy of the individual who is the providing person of the data.

BRIEF DESCRIPTION OF THE DRAWINGS

FIG. 3 is an example of privacy protection condition information according to the present invention;

FIG. 4 is an example of usage condition information according to the present invention;

FIG. 7 is an example of a permission table according to the present invention;

FIG. 12 is an example of a display screen according to the present invention.

DESCRIPTION OF THE PREFERRED EMBODIMENTS

<Overview>

Figure 1:
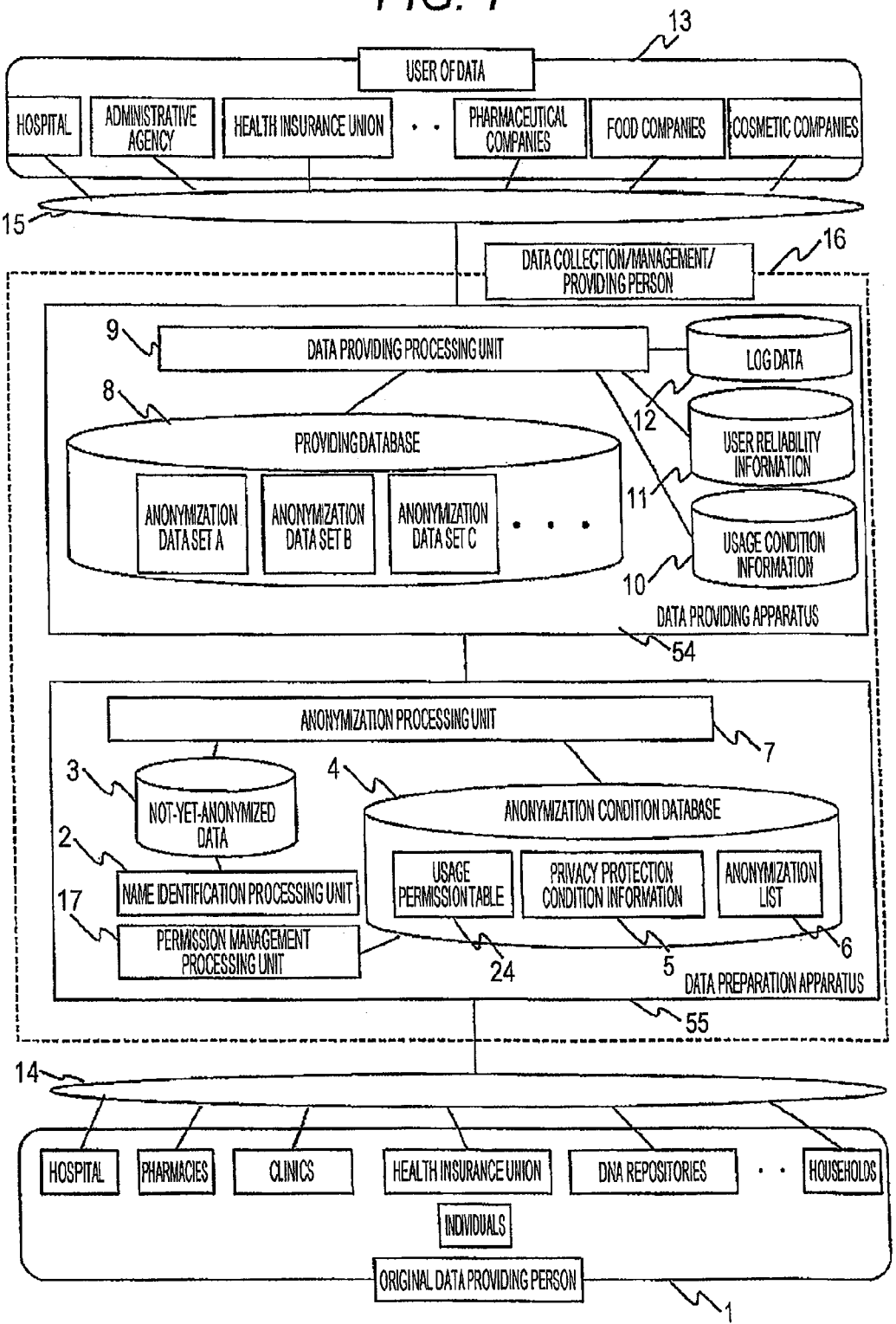
FIG. 1 is an embodiment of a schematic configuration of a privacy protection-type data providing system that prepares multiple information-providing data sets according to the present invention.
Figure 11:
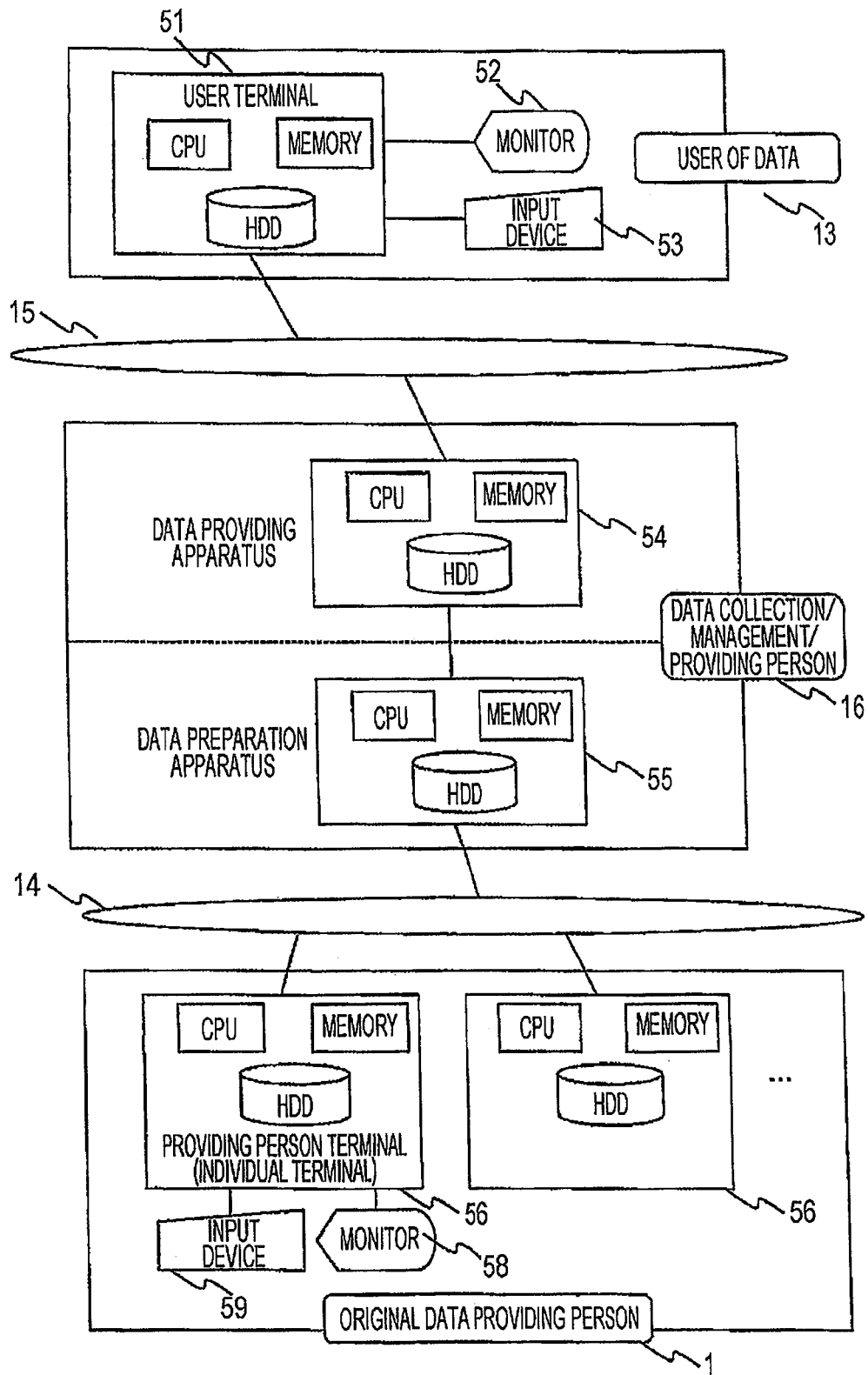
FIG. 11 is an example of a hardware configuration according to the present invention.

In an embodiment according to the present invention, first, an overview of a system where healthcare data are considered will be explained with reference to FIGS. 1, 11.

In the present embodiment, an original data providing-person 1 is considered to be an organization such as hospitals, pharmacies, clinics, health insurance union, DNA repositories, and households that manage health care data. However, since the healthcare data originally belong to an individual, the original data providing-person 1 is considered to be an individual himself/herself, and healthcare data may be directly collected from an individual.

The healthcare data about individuals accumulated in a computer (reference numeral 56 in FIG. 11) provided in a hospital and the like are collected by a data preparation apparatus (reference numeral 55 in FIG. 11) of a data collection/management/providing-person 16 via a network 14. At this occasion, data of a person exist over multiple original data providing persons, and therefore, the data are subjected to name identification performed by a name identification processing unit 2 executed by the CPU of the data preparation apparatus 55, and are stored to the HDD as not-yet-anonymized data 3. The collection of the data from the original data providing-person 1 may be performed every time the data are updated by the original data providing person, or the updated data for one day may be collected at night once a day. Alternatively, the original data may be sent from a terminal at the original data providing person, or the data may be retrieved by the data preparation apparatus.

The HDD of the data preparation apparatus 55 stores an anonymization condition database 4. This database stores a privacy protection requirement 5 and an anonymization list 6, and using this information, an anonymization processing unit 7 executed by the CPU of the data preparation apparatus 55 performs the anonymization of the personal information included in the data, whereby data provided to a user of the data 13 are generated, and the data are saved to a providing database 8 of the data providing apparatus (reference numeral 54 in FIG. 11).

The providing database 8 of the HDD of the data providing apparatus 54 stores data set that is anonymized by the anonymization processing unit 7 in accordance with multiple conditions. On the basis of usage condition information 10 and user reliability information 11, a data providing processing unit 9 executed by the data providing apparatus 54 presents, to the user of the data 13, a data set that can be provided in accordance with the total reliability, the overview thereof (data field types, the amount of data, a k value, information loss amount), and the price.

The user of the data 13 selects the data set that the user of the data 13 is going to use in accordance with the purpose of usage on the basis of the conditions presented on a monitor (reference numeral 52 in FIG. 11) connected to the user terminal of the user of the data (reference numeral 51 in FIG. 11), and receives the data from the data providing processing unit 9 via a network 15. At this occasion, the history information is recorded to log data 12. In this case, the user of the data 13 includes organization that mainly has public role such as hospitals, administrative agencies such as Public Health Center and Ministry of Health, Labor and Welfare, and health insurance unions, but also private companies such as pharmaceutical companies, food companies, and cosmetic companies <Privacy Protection Condition Information>

FIG. 3 illustrates an example of privacy protection condition information 5. A condition for protecting the privacy of an individual who is an owner of personal information included in data is set in the privacy protection condition information 5. This condition relies on laws and guidelines, and therefore, the definition may be different depending on countries, and may change depending on era. In such case, multiple pieces of privacy protection condition information may be prepared. For example, when data of the providing database 8 are provided via the data providing processing unit 9 to users of the data 13 in multiple countries, the privacy protection condition information 5 corresponding to the country from which the user of the data 13 is accessing may be selected and the provided data may be changed accordingly. However, in the present embodiment, an example will be explained in a case where there is a single piece of privacy protection condition information 5.

The data field types treated as personal information are set in the personal information range. The data field types which are not provided to the user of the data are set in the deletion item in order to protect the privacy of the individuals. The data field types of which contents are converted and provided to the user of the data are set in the conversion item. In the example of FIG. 3, the conversion item is not set, but, for example, in a case where the data can be provided while the privacy is protected if the ID for identifying an individual is changed to another ID, the ID can be set as the conversion item. The data field types that may be provided to the user of the data are set in the protection item when the individual privacy is protected.

A technique for providing data while the privacy is protected includes, for example, k-anonymization technique. The k-anonymization technique is a technique for protecting the privacy by ensuring that an address, an age, and the like are generalized so that there are at least k or more individuals who have the same value in a combination of data field types that have been set as the protection item, i.e., address, age, sex, the name of disease, and the name of operation.

The minimum value of k value that can be designated when the k-anonymization technique is applied is set in the minimum value of the k value. The usage permission records the link destination information about a usage permission table 24 as the information about the usage permission when the data are provided. Each of the data field types which are set as the personal information range is set in any one of the deletion item, the conversion item, and the protection item. However, a data field type which is not set as the personal information range may be set as the deletion item, the conversion item, and the protection item.

<Usage Permission Table>

FIG. 7 illustrates an example of the usage permission table 24. A usage permission condition when data are provided to a user of the data is set for each individual in this table. For example, in FIG. 7, the table classifies the total reliability of the user of the data into four levels, i.e., A to D, which are in the descending order of reliability. More specifically, users whose total reliability is 10, 9 are classified into the reliability A, users whose total reliability is 8 to 6 are classified into the reliability B, users whose total reliability is 5 to 3 are classified into the reliability C, and users whose total reliability is 2 to 0 are classified into the reliability D. For the user of the data of each reliability rank, the table records a permission condition defined by each individual indicating the degree the data are generalized in order to allow the data to be provided. For example, this indicates that a person having an ID 00001 allows a user of the data in the reliability rank A to be provided with data which are generalized by k-anonymization where k=10. In this case, the k-anonymization where k=10 indicates that there are 10 or more data having the same value in a combination of designated items as shown in K. Harada, Y. Sato and Y. Togashi, "Reducing Amount of Information Loss in k-anonymization for Secondary Use of Collected Personal Information," Proc. of SRII Global Conference 2012, pp. 61-69 explained above.

Figure 10:
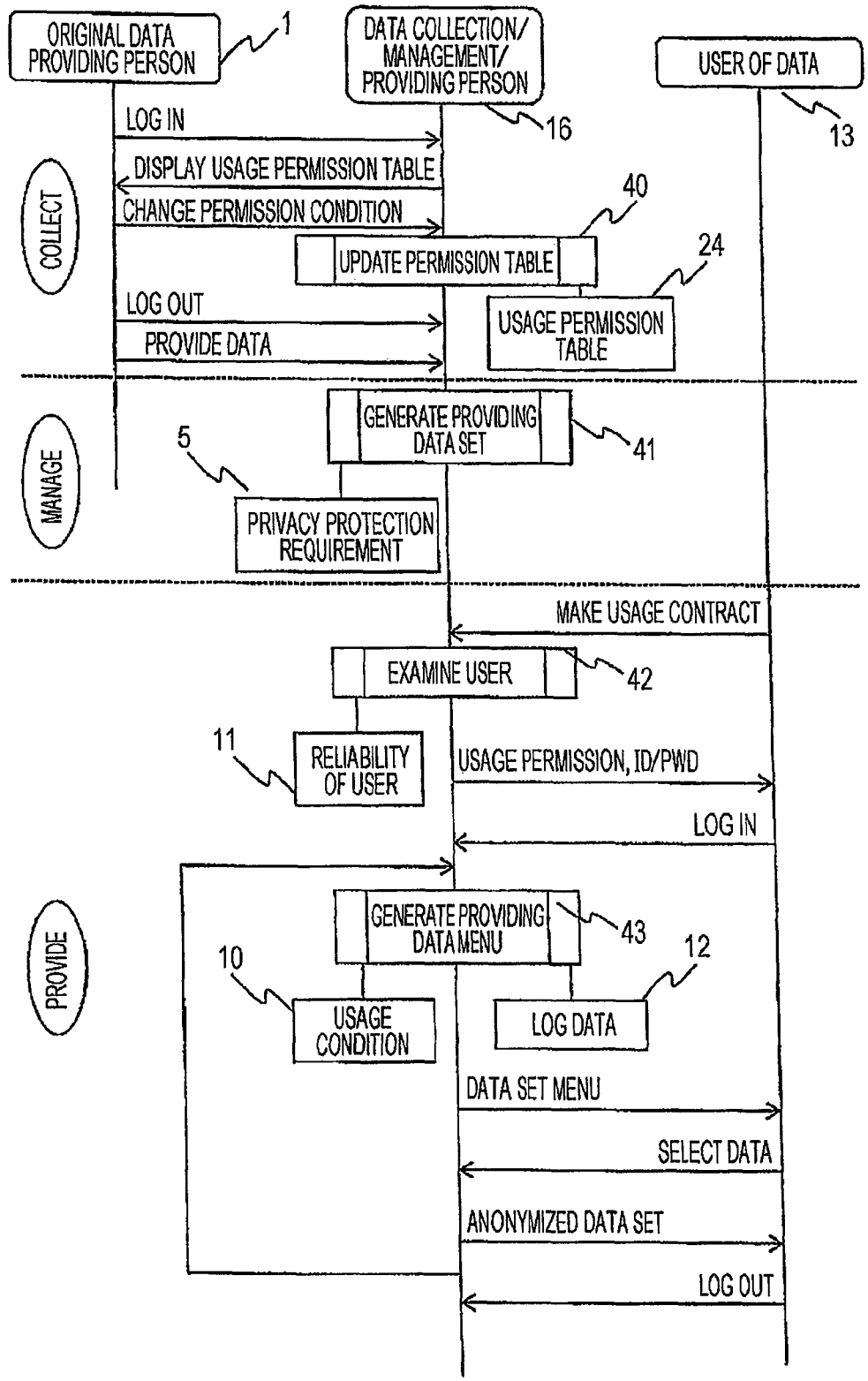
FIG. 10 is an example of a sequence utilizing the system according to the present invention.

A procedure for updating the usage permission table 24 will be shown using "collect" portion in the sequence diagram of FIG. 10. An individual who is an original data providing-person 1 uses an individual terminal 57 of FIG. 11 to log in to a permission management processing unit 17 of the data collection/management/providing-person 16 via the network 14. This permission management processing unit 17 is considered to be executed by the data preparation apparatus 55 of FIG. 11. The permission management processing unit 17 displays the usage permission table of the individual who logs in on a monitor 58 of the individual terminal 57. The individual uses an input device 59 of the individual terminal 57 to change the condition of the usage permission table. The permission management processing unit 17 updates the usage permission table 24. Finally, the individual logs out from the permission management processing unit 17.

This permission condition may be, for example, opt-out method, and accordingly, unless otherwise specified, the default condition is applied, so that the number of individuals who provide original data is ensured, and a certain level of quality, of data can be ensured. Each, individual is not only able to reject providing the original data but also able to change the permission condition, and therefore, there is an effect that a person who wishes to allow the data of himself/ herself to be used even a little can easily participate. In this case, a contact through which the permission table can be changed by an e-mail or a call center is provided as a mechanism for changing the permission table. Once the data are provided, it is difficult to delete the data, and therefore, it is preferable to make an agreement stating that data cannot be deleted even after an individual reject providing data which the individual gave usage permission in the past.

In the usage permission table 24, a value smaller than the minimum value of the k value recorded in the privacy protection condition information 5 may not be allowed to be designated. In the permission condition, permission period, the range of the permitted data, and the like may be defined as a more detailed condition.

<Providing Data Set Generating Processing>

Figure 2:
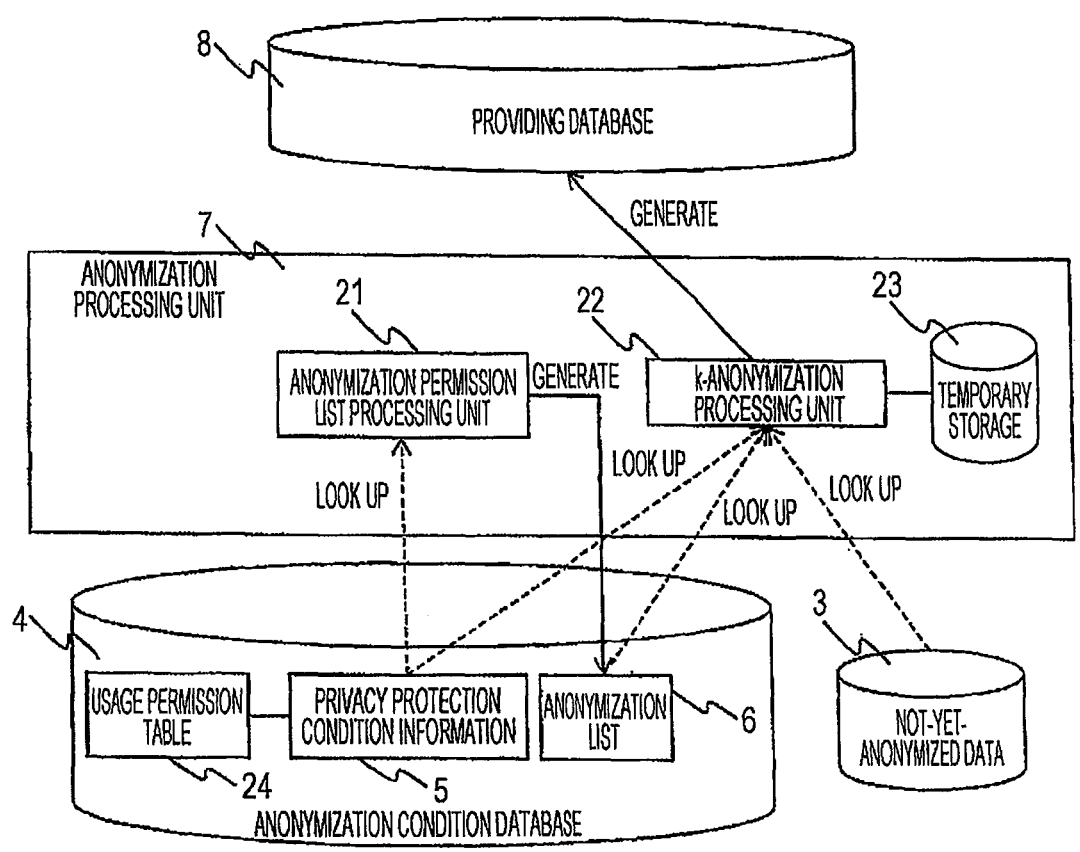
FIG. 2 is an embodiment of a detailed system mainly explaining an anonymization processing unit according to the present invention.
Figure 8:
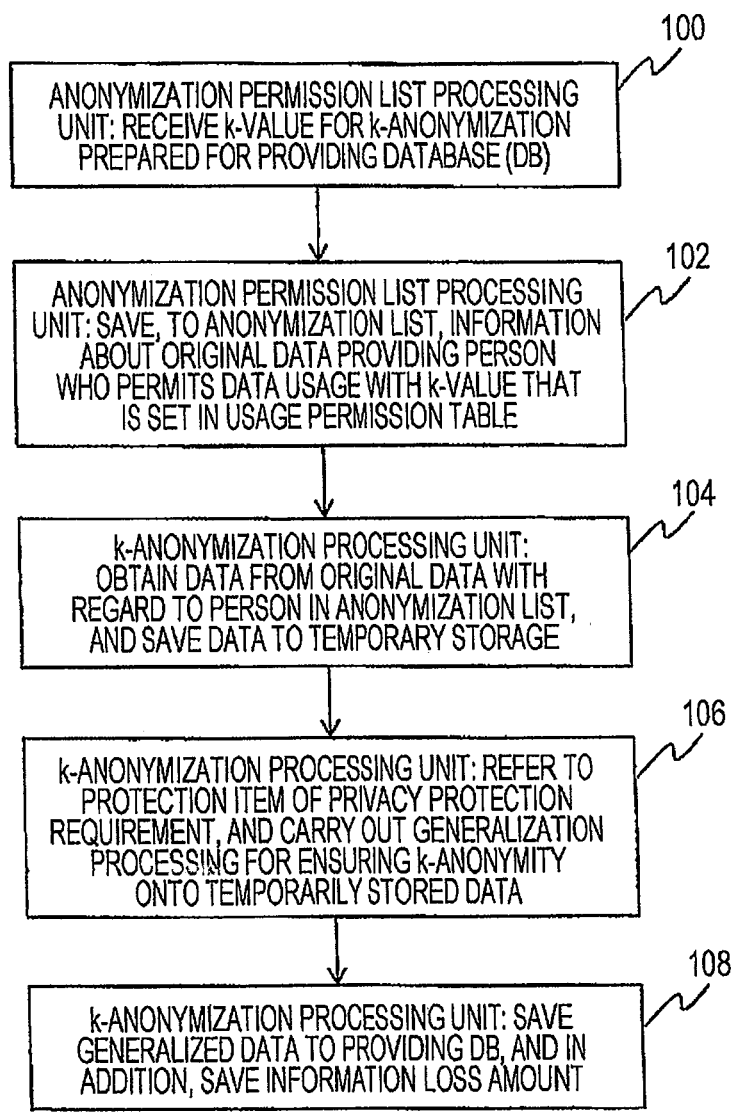
FIG. 8 is an example of a processing flow of an anonymization processing unit according to the present invention.

Subsequently, a method for generating a data set which is to be provided will be explained with reference to FIGS. 2 and 8. In the sequence diagram in FIG. 10, this processing corresponds to "generate providing data set 41" in "manage" portion. First, the data collection/management/providing-person 16 designates the k value for the k-anonymized data set prepared in the providing database 8 and transmits the designated k value to the data preparation apparatus (step 100). For example, the data set A has k=10, the data set B has k=100, and the data set C has k=500.

Subsequently, an anonymization permission list processing unit 21 looks up the usage permission table 24 with regard to the k value for each data set designated, and the anonymization permission list processing unit 21 extracts an individual who permits the data to be provided if the k value for each data set is satisfied, and generates the anonymization list 6. More specifically, in this example, where the k value for the data set is kd, and with regard to kd=10, 100, 500, the anonymization permission list processing unit 21 refers to the k value (denoted as kp) with which each individual gives permission, searches for an ID of an individual where kd>kp is satisfied, and generates an anonymization list corresponding to the value of each kd (step 102). The anonymization permission list processing unit 21 may extract an individual who permits the data to be provided on condition of the designated k value (kd) and the reliability rank (A to D) as shown in FIG. 7 added thereto, and may generate an anonymization list. In this case, the data set is generated separately for each combination of the k value and the reliability rank.

Subsequently, a k-anonymization processing unit 22 refers to the anonymization list 6, obtains information about an individual matching in the list from the not-yet-anonymized data 3, and saves the information to a temporary storage 23 (step 104). Then, the k-anonymization processing unit 22 uses the k-anonymization method described in K. Harada, Y. Sato and Y. Togashi, "Reducing Amount of Information Loss in k-anonymization for Secondary Use of Collected Personal Information," Proc. of SRII Global Conference 2012, pp. 61-69 to perform the k-anonymization using the k value designated by the anonymization permission list processing unit 21. At this occasion, a combination of data ensuring k or more uses the condition recorded in the protection item of the privacy protection condition information 5 (step 106). Finally, the k-anonymization processing unit 22 records the k-anonymizated data to the providing database 8. At this occasion, the information loss amount caused by the generalization is also saved (step 108).

This processing may be performed, for example, at night once a day and the data may be updated, or may be updated in units of month or on every several minutes. It is not so frequently to perform the step 100 and step 102, and only steps 104 to 108 may be performed.

By using the above method, it is not necessary to perform the k-anonymization every time data are provided, and appropriate data can be provided in a short time in accordance with the condition of the user of the data.

<User Reliability Information>

Figures 5, 6:
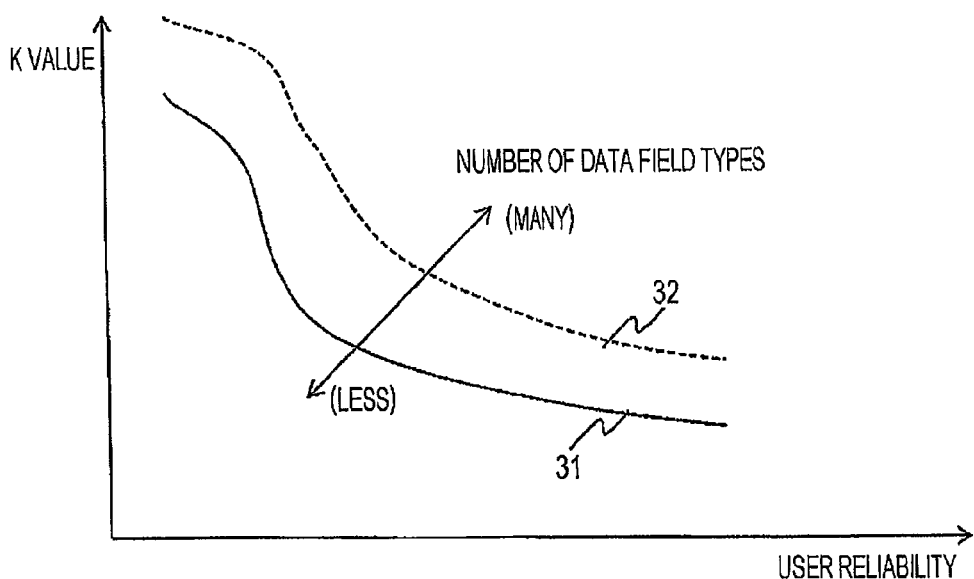
FIG. 5 is an example of user reliability information according to the present invention.
FIG. 6 is an example of graph illustrating a concept as to how to determine a k value corresponding to user reliability and usage condition according to the present invention.

FIG. 5 illustrates an example of the user reliability information 11. A value that is defined as the reliability of the user of the data is set in the user reliability information 11. The providing of data is based on the assumption that a contact has been made with the user of the data. The flow of providing of data will be explained using "provide" portion in the sequence diagram of FIG. 10. First, the user of the data 13 applies for a usage contract to the data collection/management/providing-person 16. Then, the data collection/management/providing-person 16 investigates the reliability of the user of the data, and defines the reliability as a value, and registers the value as the privacy protection condition information 5, and thereafter updates the value as necessary.

For example, in the example of FIG. 5, the total reliability is derived from the public benefit, whether or not JISQ15001: 2006 which is a standard of privacy protection has been obtained, the number of information leakage accidents, and the transaction history. For example, the total reliability is rated on a scale of 10, and the value is determined on the basis of the following distribution: the public benefit (80%)+JISQ compliance (10%)−information leakage accident (0 to 100%)+transaction history (10%). It should be noted that alternatively the scale of the reliability may employ the degree of compliance to various kinds of standard specifications and guide lines such as acquisition of privacy mark and the state of management condition.

A mechanism may be employed so that a specialized organization determines the situation of compliance to the guidelines and the public benefit. When the result of examination indicates that there would be no problem in providing the data, the data collection/management/providing-person 16 provides an ID and a password to the user of the data 13. It should be noted that an expiration date may be set for this usage permission.

In case of emergency situation such as occurrence of large scale disaster and pandemic, the user reliability information 11 may make temporary change. By using such mechanism, the data can be used for the public benefit of saving many lives.

<Usage Condition Information>

FIG. 4 illustrates an example of the usage condition information 10 which is set in accordance with the reliability of the user of the data. A condition of data that can be used by the user of the data is set in the usage condition information 10 in accordance with the total reliability. In this case, an example where the total reliability is 10 and 3 is shown. As shown in FIG. 4, when the total reliability is different, the data that can be used by the user of the data is also different.

A list of data sets according to the usage purpose is set in the purpose-dependent data set. The purpose-dependent data set may be, for example, a data set of a combination of data field types where the purpose of analyzing diabetes is assumed and a data set of a combination of data field types freely designated by the user of the data. A list of data field types included in the purpose-dependent data set is set in the data field type. The number of years for which the user of the data can obtain data is specified in the number of years data are obtained which is set for each purpose-dependent data set. The number of years data are obtained includes options, for example, a case where data are used for all the years, a case where data are used for five years, and a case where data are used for one year. Further, a list of anonymized data sets that can be provided to the user of the data and the k value and the usage price of each anonymized data set are set for each of the numbers of years data are obtained.

This setting method may be any method, but the value of the k value with which the data can be provided is preferably only those with higher values for the user of the data of which the total reliability is low, and the usage price is preferably set at a high price. Therefore, for example, the function as shown in FIG. 6 is used, so that the higher the reliability is, the lower the k value is set, and the greater the number of data field types is, the higher the risk of identifying an individual becomes, and therefore, the k value is preferably set at a high value.

<Data Providing Processing>

Figure 9:
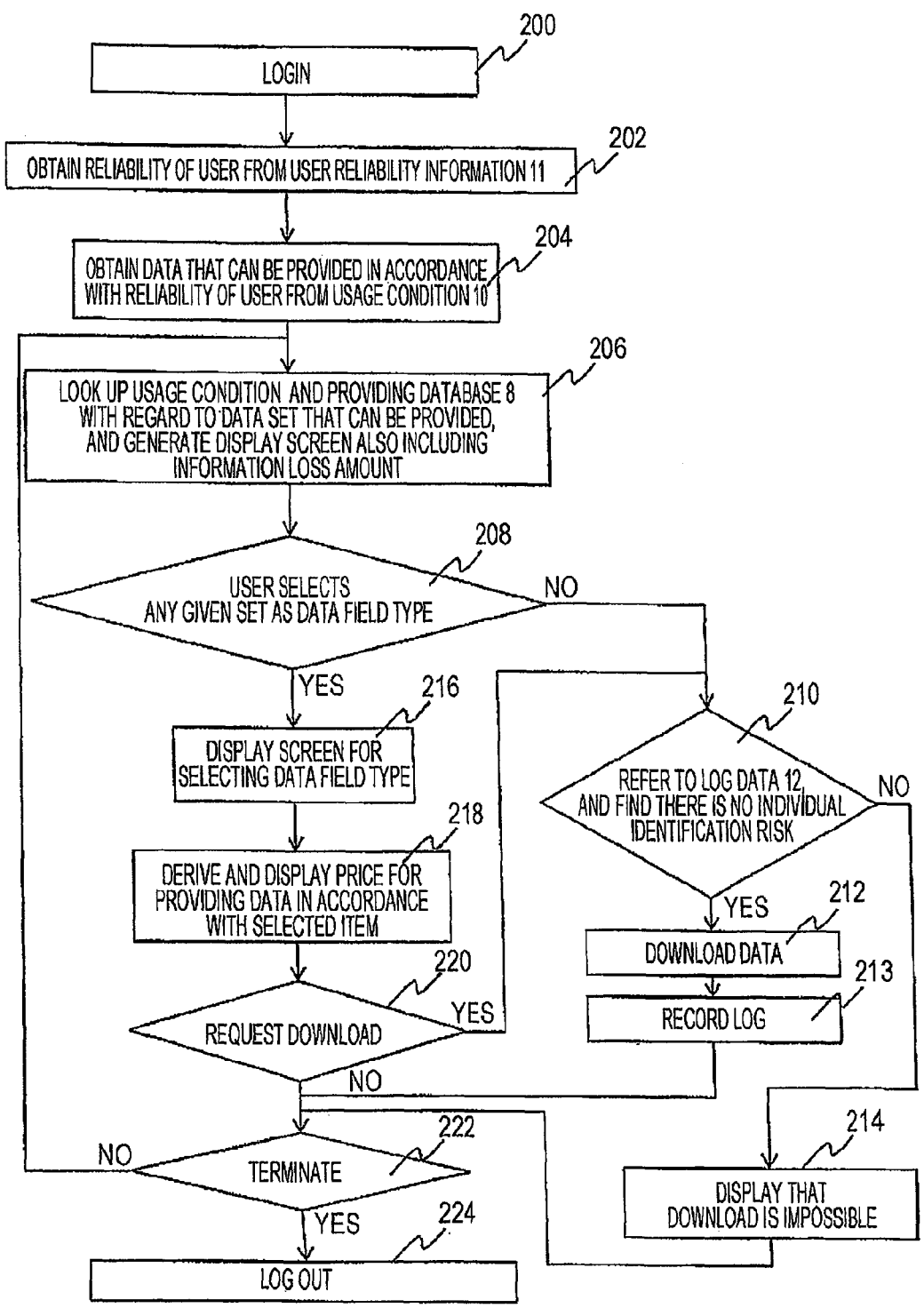
FIG. 9 is an example of a processing flow of a data providing processing unit according to the present invention.

According to the above embodiments, the data which are to be provided are prepared, and therefore, subsequently, the data providing processing will be explained with reference to FIG. 9. This case shows an example where the data providing processing unit 9 refers to the usage condition information 10 to the user reliability information 11, and data are provided via the network 15 to the user of the data 13. This procedure corresponds to processing of "provide" portion in the sequence diagram of FIG. 10.

The user of the data 13 logs in to the data providing processing unit 9 of the data providing apparatus 54 via the user terminal 51 (step 200). The data providing processing unit 9 refers to the user reliability information 11, and obtains the value of the total reliability of the user of the data 13 who logs in (step 202), and obtains the usage condition information 10 matching the value (step 204). At this occasion, as shown in FIG. 12, the information loss amount of each data set recorded in the providing database 8 is obtained, and is displayed on the monitor 52 of the user terminal 51, so that the user of the data can use the information as a material for determining which data set is to be used (step 206). As shown in FIG. 12, sample data may be displayed on the monitor 52 of the user terminal 51.

The user of the data 13 selects a data set which the user is going to use from among the specified data sets displayed on the monitor 52, and transmits information about the selected data set via the user terminal 51 to the data providing apparatus. At this occasion, depending on the total reliability of the user of the data, any given set of data field types can be selected. When the data providing processing unit 9 receives information about the data set selected with the user terminal, a determination is made as to whether a set of data field types is selected or not (step 208).

When a set of data field types is determined not to be selected, the data providing processing unit 9 refers to the log data 12 to check the data providing history in the past, and by comparing the data set provided in the past with the data set provided this time, the data providing processing unit 9 determines whether there is any risk that personal information is identified (step 210).

For example, in a case where data of which k is 10 are provided in the past with the same data field types, and data of which k is 11 are newly provided, then a difference therebetween is derived. In such case, if the data change for only one person, it is determined that the risk of identifying an individual exists. When the result indicates that there is a risk, a message indicating that downloading of data is impossible is displayed (step 214), subsequently step 222 is performed. When it is determined that there is no risk of identifying an individual, a command for allowing data to be downloaded is transmitted to the user terminal (step 212). When there is a risk of identifying the personal information, downloading may not be prohibited, and the amount of data provided may be reduced.

Then, the data providing processing unit 9 records the information to the log data 12 (step 213), and proceeds to step 222. This log is used as one of pieces of basic information for updating charge information and the reliability of the user of the data. Back to step 208, a case where the user of the data 13 selects a set of data field types will be explained. The data providing processing unit 9 displays a screen for selecting data field types on the monitor 52 of the user terminal 51 (step 216). When the user of the data 13 selects desired data field types, the user terminal 51 transmits the selected data field types to the data preparation apparatus 55.

The data providing processing unit 9 displays the price for providing the data in accordance with the number of data field types received (step 218). When the user of the data 13 is satisfied with the given condition (step 220), a data download command is transmitted from the user terminal 51 to the data preparation apparatus 55 (step 210). When the user of the data inputs a command for "not downloading" into the user terminal 51, a screen for prompting to make a selection as to whether the processing is to be terminated or not is displayed on the monitor 52 of the user terminal 51 (step 222).

When a command for "not terminating the processing" is input into the user terminal, the processing in step 206 is performed back again. When the command for terminating the processing is input into the user terminal 51, the data providing processing unit 9 having received the command from the usage terminal causes the user of the data to log out (step 224).

According to the above embodiment, the quality of the data provided is guaranteed while maintaining the privacy protection upon allowing the manager of the data to set a certain limitation, so that the convenience for the user of the data can be improved.

The data sets prepared under multiple conditions in advance are provided, so that the amount of information provided can be controlled in accordance with the character of the user of the data, whereby the safety can be improved. Further, the user of the data can also select a data set having a sufficient amount of information suitable for the usage and purpose of the user, and it is possible to avoid the risk in a case where the information is leaked.

The above example is merely one of embodiments, and the embodiment is not limited only thereto. A portion of the embodiment can be omitted, and a combination can be changed without deviating from the gist of the present invention.

What is claimed is:

1. An information providing apparatus connected to a plurality of first user terminals and a plurality of second user terminals, wherein the information providing apparatus is configured to apply anonymization processing, wherein the anonymization processing is k-anonymization processing, which is processing for converting data including personal information so that an individual is not identified, wherein the data including the personal information is collected from the plurality of first user terminals, and the information providing apparatus is configured to distribute anonymized data generated as a result of application of the anonymization processing to a respective one of the second user terminals in response to a request from the respective second user terminal, the information providing apparatus comprising:
    a storage unit configured to store:
        the data including the personal information;
        first information specifying, for each piece of data of an individual who is an owner of the personal information, a parameter, of a plurality of parameters, of the anonymized data that is allowed to be provided;
        second information specifying the personal information to which the anonymization processing is applied;
        third information specifying a level of reliability for each user associated with each respective second user terminal that receives the provided anonymized data;
        fourth information specifying a respective parameter, of the plurality of parameters, of the anonymized data which the user having the level of reliability can receive in accordance with the level of reliability; and
    a processing unit configured to:
        extract a portion of data that is allowed to be provided from among the data including the personal information for each of the plurality of parameters based on the first information;
        identify the personal information to which the anonymization processing is applied from among the personal information of the extracted portion of data based on the second information;
        execute the anonymization processing on the identified personal information with each of the plurality of parameters, thus generating a plurality of anonymized data portions, wherein the anonymized data portions have varying amounts of information;
        identify the level of reliability of the respective user of the second user terminal based on the third information in response to the request from the second user terminal; and
        identify one of the anonymized data portions to distribute to the respective second user terminal from among the plurality of anonymized data portions based on the fourth information and the level of reliability identified for the respective user.

2. The information providing apparatus according to claim 1, wherein the k-anonymization processing includes converting the data including the personal information so that one or more data field types included in the anonymized data portion have a same value, wherein a number of the data field types is equal to or more than a number designated by a corresponding parameter of the plurality of parameters.

3. The information providing apparatus according to claim 2, wherein
    the storage unit further stores log data indicating a history about providing of the anonymized data, and
    in a case where the processing unit receives a distribution request of the identified anonymized data from the second user terminal,
        the processing unit refers to the log data, and by comparing anonymized data provided in a past to the respective user of the respective second user terminal and the anonymized data for which the distribution request is received, the processing unit determines whether there is a risk of identification of personal information included in the anonymized data for which the distribution request is received, and in a case where the processing unit determines that there is the risk, the processing unit rejects the distribution request.

4. The information providing apparatus according to claim 3, wherein the first information is set in response to a request from the first user terminal.

5. The information providing apparatus according to claim 4, wherein the fourth information is set so that a value of the respective parameter specified by the fourth information decreases in response to an increase in the level of reliability for the respective user.

6. A control method for an information providing apparatus connected to a plurality of first user terminals and a plurality of second user terminals, wherein the control method for the information providing apparatus includes applying anonymization processing, wherein the anonymization processing is k-anonymization processing, which is processing for converting data including personal information so that an individual is not identified, wherein the data including the personal information is collected from the plurality of first user terminals, and distributed as anonymized data generated as a result of application of the anonymization processing to a respective one of the second user terminals in response to a request from the respective second user terminal, wherein the control method for the information providing apparatus comprises:
    storing the data including the personal information;
    storing first information specifying, for each piece of data of an individual who is an owner of the personal information, a parameter, of a plurality of parameters, of the anonymized data that is allowed to be provided;
    storing second information specifying the personal information to which the anonymization processing is applied;
    storing third information specifying a level of reliability for each user associated with each respective second user terminal that receives the provided anonymized data;
    storing fourth information specifying a respective parameter, of the plurality of parameters, of the anonymized data which the user having the level of reliability can receive in accordance with the level of reliability;
    extracting a portion of data that is allowed to be provided from among the data including the personal information for each of the plurality of parameters based on the first information;

identifying the personal information to which the anonymization processing is applied from among the personal information of the extracted portion of data based on the second information;

executing the anonymization processing on the identified personal information with each of the plurality of parameters, thus generating a plurality of anonymized data portions, wherein the anonymized data portions have varying amounts of information;

identifying the level of reliability of the respective user of the second user terminal based on the third information in response to the request from the second user terminal; and identifying one of the anonymized data portions to distribute to the respective second user terminal from among the plurality of anonymized data portions based on the fourth information and the level of reliability identified for the respective user.

7. The control method for the information providing apparatus according to claim 6, further comprising executing the k-anonymization processing for converting the data including the personal information so that one or more data field types included in the anonymized data portion have a same value, wherein a number of the data field types is equal to or more than a number designated by a corresponding parameter of the plurality of parameters.

8. The control method for the information providing apparatus according to claim 7, further comprising:

storing, in a storage unit, log data indicating a history about providing of the anonymized data, and in a case where a processing unit receives a distribution request of the identified anonymized data from the second user terminal, referring, by a processing unit, to the log data, and by comparing anonymized data provided in a past to the respective user of the respective second user terminal and the anonymized data for which the distribution request is received, the processing unit determines whether there is a risk of identification of personal information included in the anonymized data for which the distribution request is received, and in a case where the processing unit determines that there is the risk, the processing unit rejects the distribution request.

9. The control method for the information providing apparatus according to claim 8, further comprising setting the first information in response to a request from the first user terminal.

10. The control method for the information providing apparatus according to claim 9, further comprising setting the fourth information so that a value of the respective parameter specified by the fourth information decreases in response to an increase in the level of reliability for the respective user.

* * * * *